United States Patent [19]

Saville

[11] Patent Number: Plant 5,449

[45] Date of Patent: Apr. 30, 1985

[54] ROSE PLANT—SAVANHOUR

[75] Inventor: F. Harmon Saville, Rowley, Mass.

[73] Assignee: Nor'East Miniature Roses, Inc., Rowley, Mass.

[21] Appl. No.: 535,735

[22] Filed: Sep. 26, 1983

[51] Int. Cl.[3] ..... A01H 5/00

[52] U.S. Cl. ..... Plt./10

[58] Field of Search ..... Plt./10

*Primary Examiner*—Robert E. Bagwill

*Attorney, Agent, or Firm*—Vincent G. Gioia

[57] ABSTRACT

A new miniature rose variety producing high centered flowers of bright red coloring which are long lasting on the plant and as a cut flower.

1 Drawing Figure

The present invention relates to a new and distinct variety of rose plant of the miniature rose class, which was originated by my crossing as seed parent a seedling of the cross Tamango × Yellow Jewel and the rose known as "Zinger" as pollen parent. The varietal denomination of this new variety is "Savanhour".

Among the novel characteristics possessed by this new variety which distinguish it from its parents and all other varieties of which I am aware are high centered bright red flowers which open well and are produced on a miniature plant which grows 10 to 12 inches high with attractive clean green foliage. Flowers are long lasting on the plant and as a cut flower. Asexual reproduction by budding of the new variety as performed in Essex County, Mass., shows that the foregoing and other distinguishing characteristics come true to form and are established and transmitted through succeeding propagations.

The accompanying drawings show typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "45A" is plate 45A of The Royal Horticultural Society Colour Chart.

Parentage: Seedling.

*Seed parent.*—Seedling [Tamango × Yellow Jewel].

*Pollen parent.*—"Zinger".

Class: Miniature.

The following observations are made of specimens grown outdoors in Essex County, Mass. during the month of July.

FLOWER

Blooming habit: Recurrent.

Bud:

(1) *Size.*—Medium.

(2) *Form.*—Ovate.

(3) *Color.*—When sepals first divide — near 45A. When petals begin to unfurl — 45A to 45B.

(4) *Sepals.*—Slightly foliated, longer than bud.

(5) *Peduncle.*—Length — $\frac{3}{4}$ to 1 inch. Aspect — straight. Strength — erect. Color — near 144B.

Bloom:

(1) *Size.*—Average size when fully expanded — about 1 to $1\frac{1}{4}$ inches.

(2) *Borne.*—Singly.

(3) *Form.*—High centered at first, becoming flat; petals reflex and roll under as flower opens.

(4) *Petalage.*—Number of petals under normal conditions — about 18.

(5) *Color.*—Color of buds and flowers are relatively uniform and stable between 45A and 45B including petal top and bottom surfaces. Color holds even after several days and generally tonality remains the same.

Petals:

(1) *Texture.*—Thick.

(2) *Appearance.*—Inside velvety; outside satiny.

(3) *Form.*—Fan shaped.

(4) *Arrangement.*—Regularly arranged, shingle like.

(5) *Petaloids in center.*—Few.

(6) *Persistence.*—Drop off cleanly.

(7) *Fragrance.*—Slight.

(8) *Lasting quality.*—Very long lasting on plant and as cut flower.

REPRODUCTIVE ORGANS

Stamens, filaments and anthers:

(1) *Arrangement.*—Regularly arranged around styles.

(2) *Color.*—Near 17A.

Pollen:

*Color.*—Yellow orange.

Styles: Medium length.

Stigmas:

*Color.*—Near 8D.

Hips:

*Shape.*—Oval.

*Size.*—Medium.

*Color.*—Orange red.

*Do seeds protrude?*—No.

PLANT

Form: Spreading, bushy.

Growth: Uniform branching.

*Height attained.*—About 10 to 12 inches.

Foliage: Compound 5 to 7 leaflets.

(1) *Size.*—Medium.

(2) *Quantity.*—Abundant.

(3) *Color.*—New foliage: Upper side — near to 147B. Under side — near to 148C. Old foliage: Upper side — near 137A. Under side — near 148B.

(4) *Shape.*—Oval to elliptic.

(5) *Texture.*—Upper side is glossy and under side is matte.

(6) *Edge.*—Serrated.

(7) *Serration.*—Uniform.

(8) *Leaf stem.*—Color — near to 136C. Under side — near 143C.

(9) *Stipules.*—Medium length.

(10) *Resistance to disease.*—Blackspot — average. Mildew — average. Rust — average.

Wood:

(1) *New wood.*—Color — near 138A. Bark — smooth.

(2) *Old wood.*—Color — near 141C. Bark — smooth.

Thorns:

(1) *Thorns.*—Quantity (main stalk): average. On laterals from stalk — few. Form — short, thin, pointed, angled slightly downward. Length — medium. Color — near 156C. Position — irregular.

(2) *Prickles.*—None.

Winter hardiness: Requires ordinary protection in extreme climates.

I claim:

1. A new and distinct variety of rose plant of the miniature rose class, substantially as shown and described, characterized particularly by bright red flowers of good high centered form which open well and retain color upon aging.

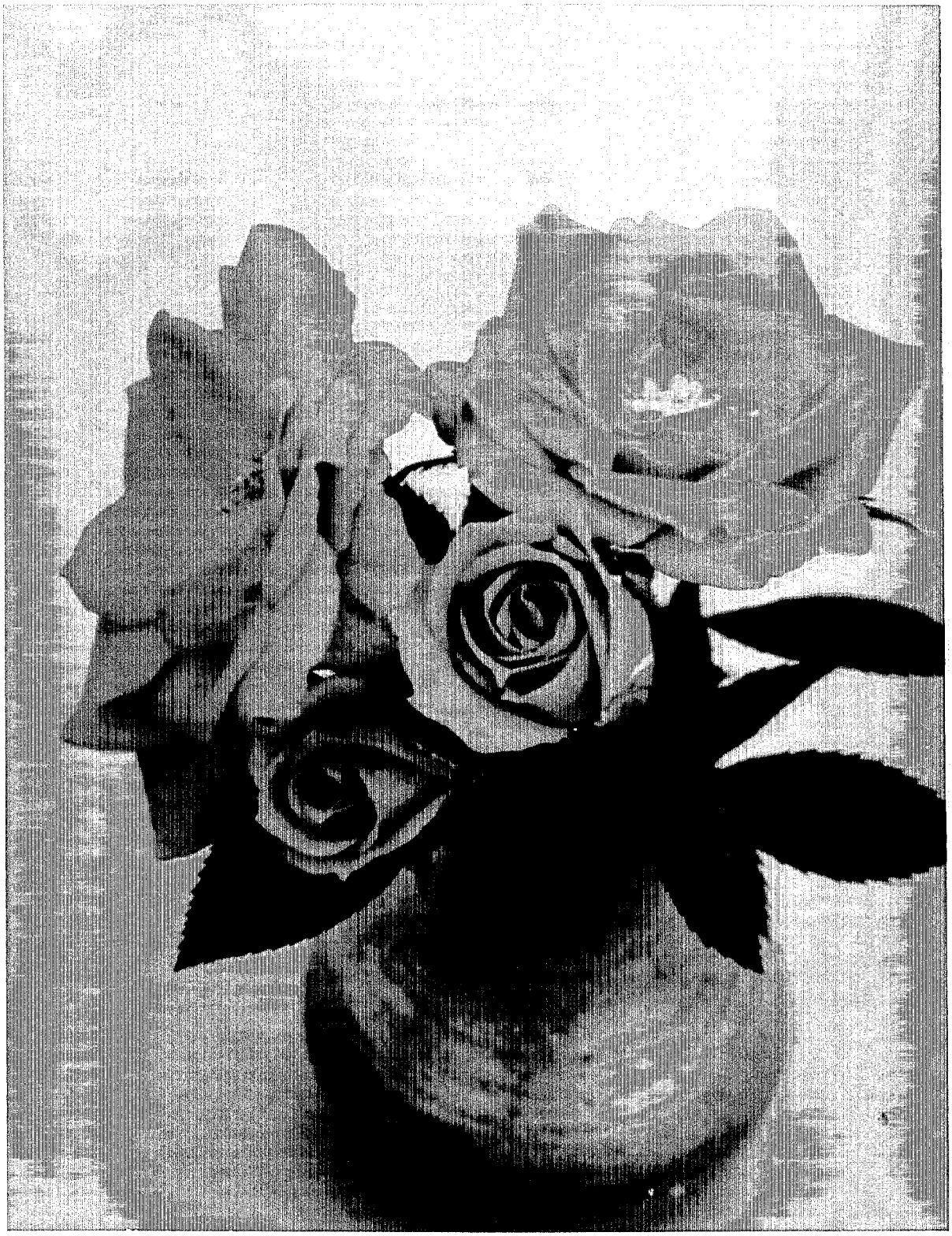

* * * * *